United States Patent
Gregerson et al.

(10) Patent No.: US 7,001,045 B2
(45) Date of Patent: Feb. 21, 2006

(54) CANTILEVERED GANTRY APPARATUS FOR X-RAY IMAGING

(75) Inventors: Eugene A. Gregerson, Bolton, MA (US); Richard K. Grant, Sudbury, MA (US); Norbert J. Johnson, North Andover, MA (US)

(73) Assignee: Breakaway Imaging, LLC, Littleton, MA (US)

( * ) Notice: Subject to any disclaimer, the term of this patent is extended or adjusted under 35 U.S.C. 154(b) by 21 days.

(21) Appl. No.: 10/459,405

(22) Filed: Jun. 11, 2003

(65) Prior Publication Data

US 2003/0235266 A1    Dec. 25, 2003

Related U.S. Application Data

(60) Provisional application No. 60/388,063, filed on Jun. 11, 2002.

(51) Int. Cl.
  *F21V 33/00*    (2006.01)
(52) U.S. Cl. .................. 362/253; 378/197; 378/198
(58) Field of Classification Search .............. 362/89, 362/253; 378/193, 195–198
See application file for complete search history.

(56) References Cited

U.S. PATENT DOCUMENTS

| | | |
|---|---|---|
| 3,549,885 A | 12/1970 | Andersson |
| 3,617,749 A | 11/1971 | Massiot |
| 4,200,799 A | 4/1980 | Saito |
| 4,352,986 A | 10/1982 | Pfeiler |
| 4,442,489 A | 4/1984 | Wagner |
| 4,481,656 A | 11/1984 | Janssen et al. |
| 4,741,015 A | 4/1988 | Charrier |
| 4,803,714 A | 2/1989 | Vlasbloem |
| 4,810,881 A | 3/1989 | Berger et al. |
| 4,829,252 A | 5/1989 | Kaufman |
| 4,875,228 A | 10/1989 | Archer |
| 4,884,293 A | 11/1989 | Koyama |
| 4,935,949 A | 6/1990 | Fujita et al. |

(Continued)

FOREIGN PATENT DOCUMENTS

DE    G 89 05 588.8    9/1990

(Continued)

OTHER PUBLICATIONS

SIREMOBIL Iso-$C^{3D}$ Breathtaking Views in the OR!, SIEMENS, Siemens Aktiengesellschaft Medical Solutions Henkestrasse 127, D-91052 Erlangen, pp. 1-16, no date given.

(Continued)

*Primary Examiner*—Stephen F Husar
(74) *Attorney, Agent, or Firm*—Hamilton, Brook, Smith & Reynolds, P.C.

(57) ABSTRACT

An x-ray scanning imaging apparatus with a rotatably fixed generally O-shaped gantry ring, which is connected on one end of the ring to support structure, such as a mobile cart, ceiling, floor, wall, or patient table, in a cantilevered fashion. The circular gantry housing remains rotatably fixed and carries an x-ray image-scanning device that can be rotated inside the gantry around the object being imaged either continuously or in a step-wise fashion. The ring can be connected rigidly to the support, or can be connected to the support via a ring positioning unit that is able to translate or tilt the gantry relative to the support on one or more axes. Multiple other embodiments exist in which the gantry housing is connected on one end only to the floor, wall, or ceiling. The x-ray device is particularly useful for two-dimensional multi-planar x-ray imaging and/or three-dimensional computed tomography (CT) imaging applications

29 Claims, 8 Drawing Sheets

U.S. PATENT DOCUMENTS

| | | |
|---|---|---|
| 4,955,046 A | 9/1990 | Siczek et al. |
| 4,987,585 A | 1/1991 | Kidd et al. |
| 5,014,292 A | 5/1991 | Siczek et al. |
| 5,014,293 A | 5/1991 | Boyd et al. |
| 5,032,990 A | 7/1991 | Eberhard et al. |
| D323,386 S | 1/1992 | Perusek |
| 5,084,908 A | 1/1992 | Alberici et al. |
| 5,095,501 A | 3/1992 | Kobayashi |
| 5,097,497 A | 3/1992 | Deucher et al. |
| 5,159,622 A | 10/1992 | Sakaniwa et al. |
| 5,187,659 A | 2/1993 | Eberhard et al. |
| 5,265,610 A | 11/1993 | Darrow et al. |
| 5,287,274 A | 2/1994 | Saint Felix et al. |
| D345,606 S | 3/1994 | Perusek |
| 5,319,693 A | 6/1994 | Eberhard et al. |
| 5,390,112 A | 2/1995 | Tam |
| 5,448,607 A | 9/1995 | McKenna |
| 5,448,608 A | 9/1995 | Swain et al. |
| 5,452,337 A | 9/1995 | Endo et al. |
| 5,499,415 A | 3/1996 | McKenna |
| 5,515,416 A | 5/1996 | Siczek et al. |
| 5,583,909 A | 12/1996 | Hanover |
| 5,592,523 A | 1/1997 | Tuy et al. |
| 5,625,660 A | 4/1997 | Tuy |
| 5,638,419 A | 6/1997 | Ingwersen |
| 5,661,772 A | 8/1997 | Bär et al. |
| 5,740,222 A | 4/1998 | Fujita et al. |
| 5,740,224 A | 4/1998 | Müller et al. |
| 5,745,545 A | 4/1998 | Hughes |
| 5,784,428 A | 7/1998 | Schmidt |
| 5,802,138 A | 9/1998 | Glasser et al. |
| 5,912,943 A | 6/1999 | Deucher et al. |
| RE36,415 E | 11/1999 | McKenna |
| 6,041,097 A | 3/2000 | Roos et al. |
| 6,147,352 A | 11/2000 | Ashburn |
| 6,203,196 B1 | 3/2001 | Meyer et al. |
| 6,212,251 B1 | 4/2001 | Tomura et al. |
| 6,289,073 B1 | 9/2001 | Sasaki et al. |
| 6,322,251 B1 | 11/2001 | Ballhaus et al. |
| 6,324,246 B1 | 11/2001 | Ruimi |
| 6,325,537 B1 | 12/2001 | Watanabe |
| 6,442,235 B1 | 8/2002 | Koppe et al. |
| 6,484,049 B1 | 11/2002 | Seeley et al. |
| 6,487,267 B1 | 11/2002 | Wolter |
| 6,496,558 B1 | 12/2002 | Graumann |
| 6,519,312 B1 | 2/2003 | Tybinkowski et al. |
| 6,546,068 B1 | 4/2003 | Shimura |
| 6,590,953 B1 | 7/2003 | Suzuki et al. |
| 6,609,826 B1 * | 8/2003 | Fujii et al. ................. 378/198 |
| 2001/0005410 A1 | 6/2001 | Rasche et al. |
| 2002/0118793 A1 | 8/2002 | Horbaschek |
| 2002/0168053 A1 | 11/2002 | Schomberg |
| 2003/0072416 A1 | 4/2003 | Rasche et al. |

FOREIGN PATENT DOCUMENTS

| | | |
|---|---|---|
| DE | 195 35 583 A1 | 3/1997 |
| DE | 198 39 825 C 1 | 10/1999 |
| DE | 199 27 953 A1 | 1/2001 |
| EP | 0 471 455 A2 | 7/1991 |
| EP | 0 564 292 A2 | 10/1992 |
| EP | 0 564 292 A2 | 10/1993 |
| EP | 0 810 005 A2 | 12/1997 |
| EP | 1 090 585 A1 | 4/2001 |
| FR | 2 304 321 | 10/1976 |
| GB | 2 088 670 A | 6/1982 |
| WO | WO 96/06561 | 3/1996 |

OTHER PUBLICATIONS

Ning, R., et al., "An Image Intensifier-Based Volume Tomographic Angiography Imaging System", *SPIE* vol. 3032, pp. 238-247.

Chabbal, J., et al., "Amorphous Silicon X-Ray Image Sensor", *Physics of Medical Imaging*, Proceedings of SPIE, Feb. 23-25, 1997, vol. 3032, 14 pgs.

Hsiung, H., et al., "3D x-ray angiography: Study of factors affecting projection data consistency", *Physics of Medical Imaging*, Proceedings of SPIE, pp. 226-237, Feb. 23-25, 1997, vol. 3032.

Lwata, K., et al., "Description of a Prototype Combined CT-SPECT System with a Single CdZnTE Detector", *Nuclear Science Symposium Conference Record*, 2000 IEEE, XP010556613, pp. 16-1-16-5.

Lang, T.F., et al., "A Prototype Emission-Transmission Imaging System", *Proceedings of the Nuclear Science Symposium and Medical Imaging Conference*, 1991 IEEE, XP010058199, pp. 1902-1906.

Lang, Thomas, F., et al., "Description of a Prototype Emission—Transmission Computed Tomography Imaging System", *Journal of Nuclear Medicine, Society of Nuclear Medicine*, 1992, XP002901050, pp. 1881-1887.

\* cited by examiner

CANTILEVERED GANTRY APPARATUS FOR X-RAY IMAGING

RELATED APPLICATION

This application claims the benefit of U.S. Provisional Application No. 60/388,063, filed Jun. 11, 2002, the entire teachings of which are incorporated herein by reference.

BACKGROUND OF THE INVENTION

Healthcare practices have shown the tremendous value of three-dimensional imaging, mainly as a diagnostic tool in the Radiology Department. Other areas of care, including the operating room, intensive care departments and emergency departments, rely on two-dimensional imaging (fluoroscopy, ultrasound, 2-D mobile X-ray) as the primary means of diagnosis and therapeutic guidance. This is mainly due to the cost, size, and expertise required to operate traditional three-dimensional devices. Moreover, radiologic quality CT scanners have been designed to maximize image quality at the expense of mobility. Truly practical and mobile imaging solutions for "non-radiology departments" capable of performing both 2D and 3D imaging in the same device have yet to be developed. Previous attempts simply do not address the true need, which is to maintain a sizable volume while meeting a level of expected image quality. In the past, there have been two types of devices proposed to address this need. One type of device uses a mobile C-arm and spins it around the anatomy, such as the Siremobil Iso-C$^{3D}$ system from Siemens AG. These C-arm based attempts have a limited field of view, are procedurally cumbersome and have an inherent limit to the image quality.

Others have attempted to make a fixed-bore CT mobile, such as the device described in Butler W. E. et al, A Mobile CT Scanner with Intraoperative and ICU Application, 1998. (http://neurosurgery.mgh.harvard.edu/mobileCT.htm). However, these so-called "mobile CT scanners" are characterized by the elevated dosing level of a traditional fixed CT scanner, they are difficult to maneuver, and they are incapable of performing 2D imaging when that is all that is needed.

In general, the fluoroscopic C-arm attempts meet the criteria of mobility and flexibility, but fall short on image quality and image volume. The "mobile CT scanner" attempts meet the criteria of image volume and quality, but fail to address the practical issues of usability and cost. Additionally, state of the art CT scanners are incapable of translating and tilting in the same fashion of mobile fluoroscopy systems.

A truly mobile and practical solution for 'non-radiology department' 3-D imaging also capable of performing 2D imaging does not yet exist. This is mainly due to the fact that current tomographic scanners are not mobile in a practical manner. The inability to move a CT scanner with the same degrees of freedom of mobile C-arms has hindered the acceptance and use of mobile three-dimensional imaging. This has limited the value of three-dimensional computed tomographic imaging to areas mainly as a diagnostic tool in the Radiology Department.

There is a need for a mobile CT scanner for use in the operating room, intensive care unit, emergency room and other parts of the hospital, in ambulatory surgery centers, physician offices, and the military battlefield, which is truly mobile and capable of performing both 2D and 3D x-ray imaging.

SUMMARY OF THE INVENTION

The present invention is directed to an imaging apparatus comprising a generally O-shaped gantry ring having an x-ray source and a detector. The gantry ring is rigidly or movably secured on one side of the ring to a support structure, such as a mobile cart, a wall, a ceiling, a floor, or a patient table, in a cantilevered fashion.

According to one aspect, a positioner assembly can secure the gantry ring to the support structure in a cantilevered fashion, the positioner assembly permitting the gantry to translate in at least one direction, and/or rotate around at least one axis, relative to the support structure.

According to one aspect, the x-ray source is contained inside the gantry ring, opposed to a detector array. The x-ray source (and optionally the detector) can rotate around the inside of the gantry ring, preferably through a full or partial 360 degree scan around the interior of the gantry. The imaging apparatus is particularly advantageous for medical imaging applications, including 3D computerized tomographic (CT) imaging and 2D x-ray radiographic scanning, as well as other medical, scientific, and industrial applications.

According to another aspect, a method for imaging an object with an imaging system having a substantially O-shaped gantry secured to a support structure in a cantilevered fashion by a ring positioning unit, comprises positioning the object within a central opening of the generally O-shaped gantry; operating the ring positioning unit to position the gantry at a predetermined position and orientation relative to the support structure; and obtaining an image of the object.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

Figure 1:
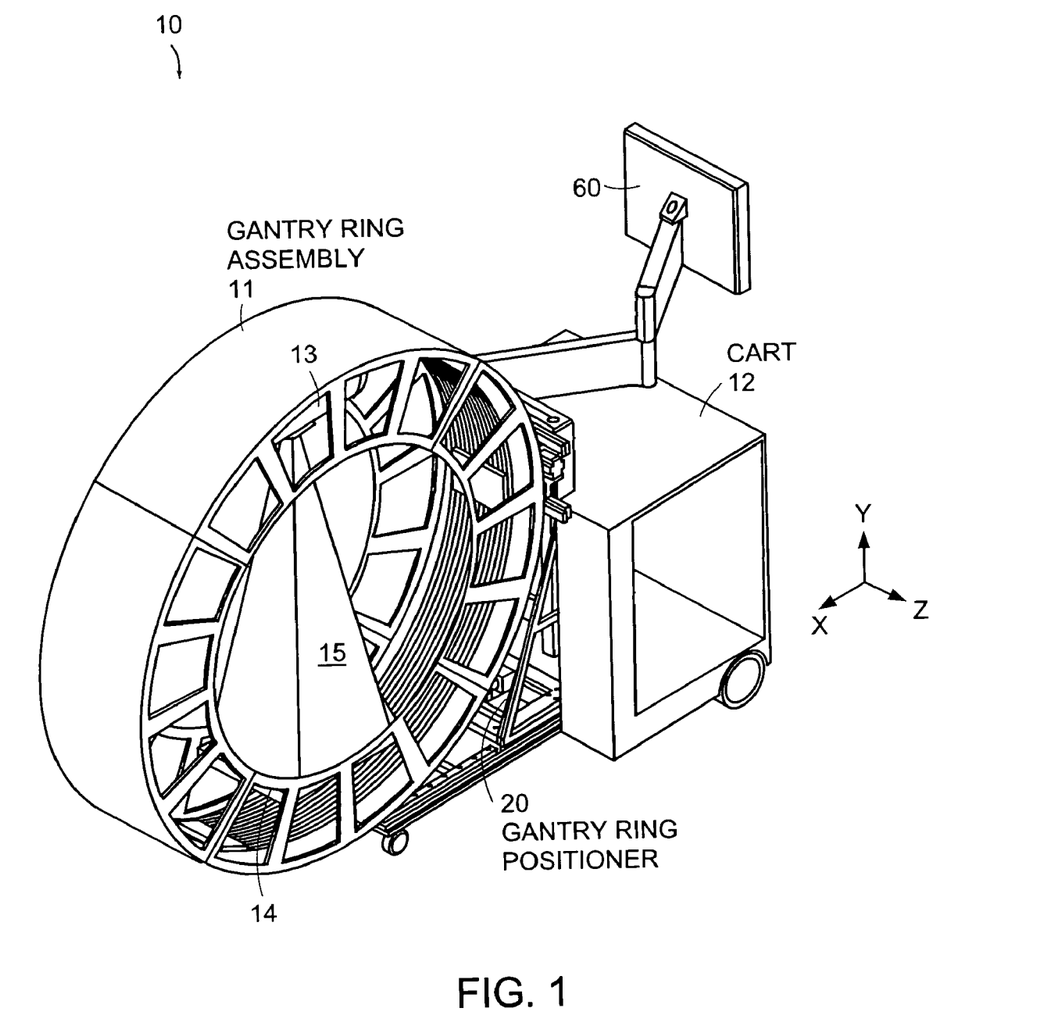
FIG. 1 is a schematic diagram of a mobile x-ray scanning system with a cantilevered O-shaped gantry according to one embodiment of the invention.

FIG. 1 is a schematic diagram showing an x-ray scanning system 10 in accordance with one embodiment of the invention. The x-ray scanning system 10 includes a gantry 11 secured to a support structure, which could be a mobile or stationary cart, a patient table, a wall, a floor, or a ceiling. As shown in FIG. 1, the gantry 11 is secured to a mobile cart 12 in a cantilevered fashion via a ring positioning unit 20. As described in further detail below, the ring positioning unit 20 can translate and/or tilt the gantry 11 with respect to the support structure to position the gantry 11 in any number of imaging positions and orientations.

The mobile cart 12 of FIG. 1 can optionally include a power supply, an x-ray power generator, and a computer system for controlling operation of the x-ray scanning device and for performing image processing, storage of x-ray images, or other data processing functions. In a preferred embodiment, the computer system controls the positioning unit 20 to enable the gantry 11 to be quickly moved to a particular user-defined position and orientation. The computer preferably has a memory that is capable of storing positioning information relating to particular gantry positions and/or orientations. This stored positioning information can be used to automatically move the gantry to a pre-defined configuration upon demand.

The mobile cart 12 preferably also includes a display system 60, such as a flat panel display, for displaying images obtained by the x-ray scanner. The display can also include a user interface function, such as a touch-screen controller, that enables a user to interact with and control the functions of the scanning system. In certain embodiments, a user-controlled pendant or foot pedal can control the functions of the scanning system.

It will be understood that one or more fixed units can also perform any of the functions of the mobile cart 12.

According to one aspect, the x-ray scanning system of the invention can be used to obtain two-dimensional planar or three-dimensional computerized tomographic (CT) x-ray images of an object, such as a patient. In the embodiment shown in FIG. 1, the gantry 11 is a generally circular, or "O-shaped," housing having a central opening into which an object being imaged is placed. The gantry 11 contains an x-ray source 13 (such as a rotating anode pulsed x-ray source) that projects a beam of x-ray radiation 15 into the central opening of the gantry, through the object being imaged, and onto a detector array 14 (such as a flat panel digital detector array) located on the opposite side of the gantry. The x-rays received at the detector 14 can then be used to produce a two-dimensional or three-dimensional image of the object using well-known techniques.

The x-ray source 13 is able to rotate around the interior of the gantry 11 in a continuous or step-wise manner so that the x-ray beam can be projected through the object, and through a common isocenter, at various angles over a partial or full 360 degree rotation. The detector array is also rotated around the interior of the gantry, in coordination with the rotation of the x-ray source, so that for each projection angle of the x-ray source, the detector array is positioned opposite the x-ray source on the gantry. The apparatus is thus able to obtain high-quality x-ray images of the targeted object in any projection plane over a partial or full 360 degree rotation.

Figure 2:
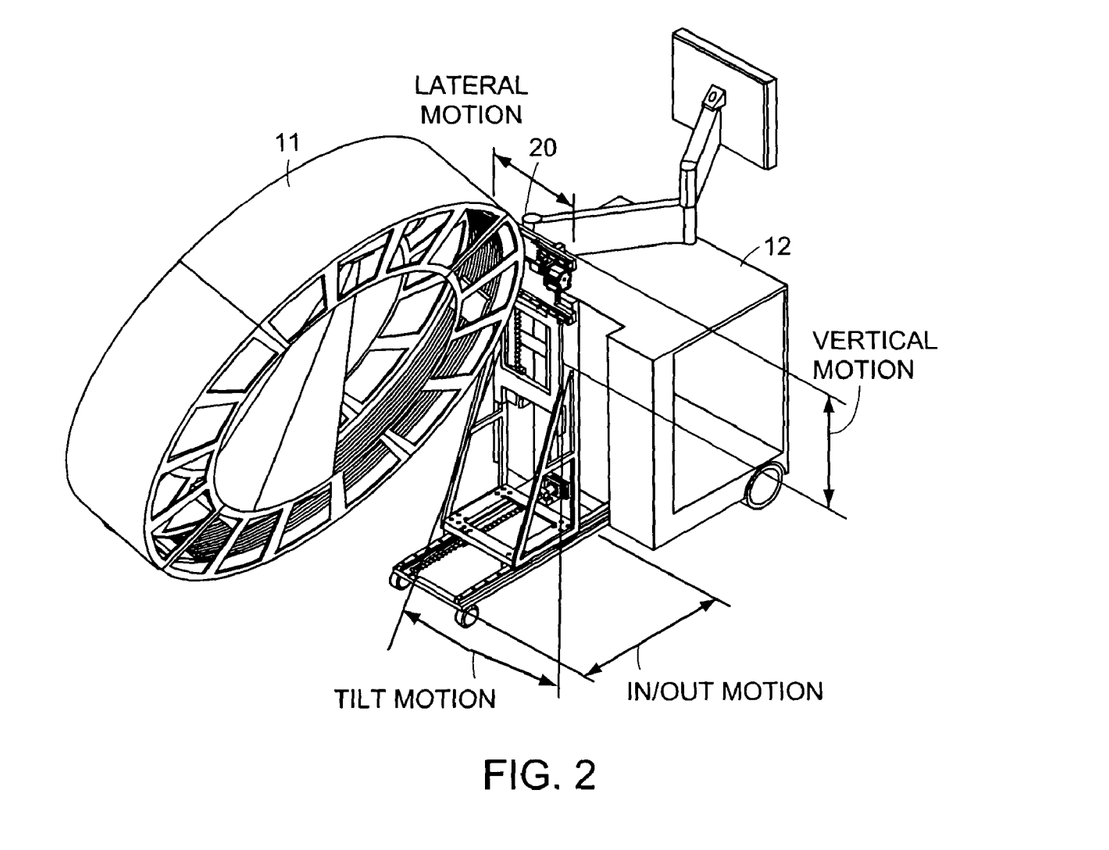
FIG. 2 shows the scanning system of FIG. 1 with the cantilevered O-shaped gantry in a translated and tilted position via a ring positioning unit.

FIG. 2 shows the scanning system of FIG. 1 with the cantilevered O-shaped gantry 11 in a translated and tilted position via a ring positioning unit 20. The positioning unit 20 connects to the gantry 12 on one side, securing the gantry to the a mobile cart 12 or other support in a cantilevered fashion. The positioning unit 20 enables the gantry 11 to translate and/or rotate with respect to the support structure, including, for example, translational movement along at least one of the x-, y-, and z-axes, and/or rotation around at least one of the x- and y-axes. As shown in FIG. 2, the positioner 20 is capable of translating the gantry 11 in three directions relative to the cart 12, including a vertical direction (i.e. up and down), an in/out direction (i.e. towards and away from the cart), and a lateral direction (i.e. along the rotational axis of the x-ray source). The positioner is also capable of tilting the gantry around one or more axes. It will be understood that various other embodiments of the invention exist where the cantilevered gantry remains fixed relative to the support structure, or where the gantry is capable of translational or tilting movement in certain directions, but not in others.

The gantry positioning unit 20 can be controlled manually, or, in a preferred embodiment, it is a motorized system that can be moved electro-mechanically to a desired position. A computerized motion control system can be attached to motorized components of the positioner and one or more discreet positions and orientations of the gantry may be stored in the computer's memory. During operation of the x-ray scanner, pre-defined gantry positions and orientations may be returned to quickly and easily.

Figure 3:
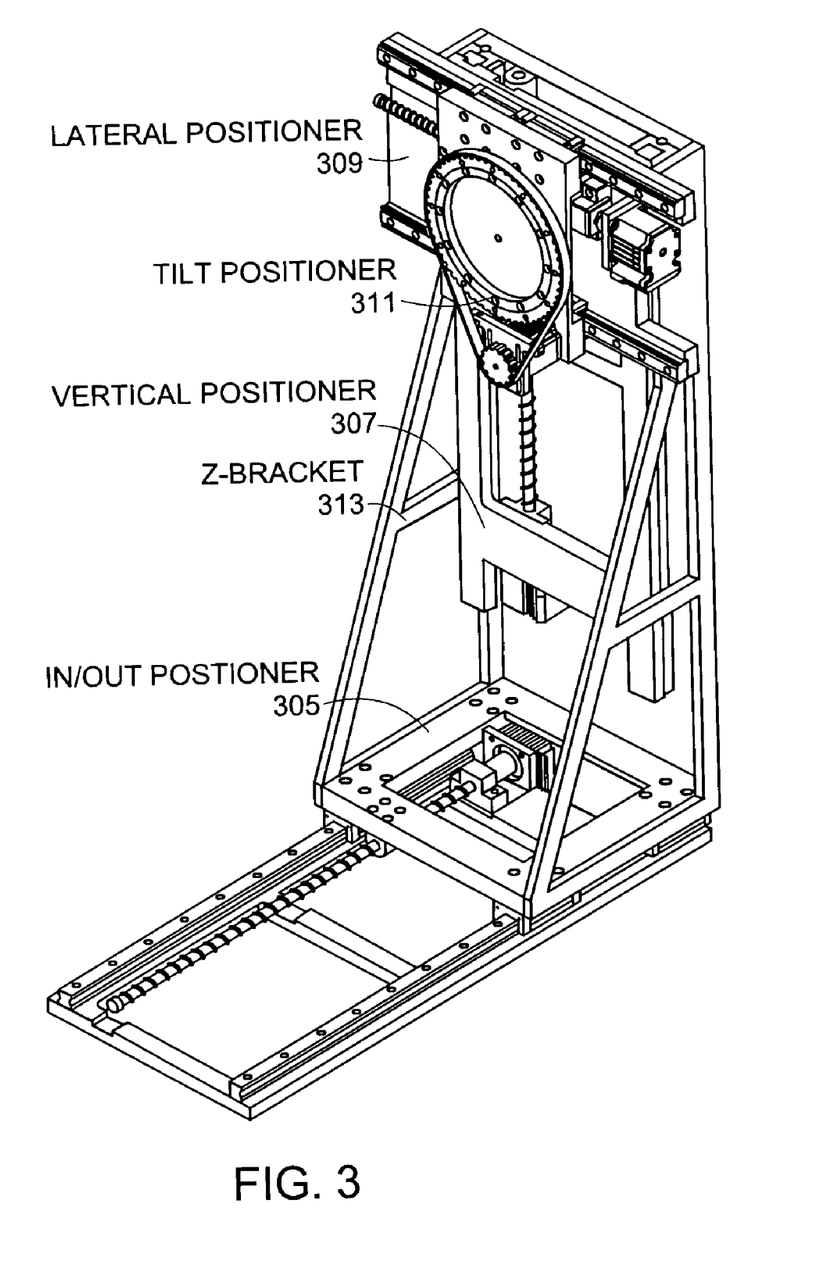
FIG. 3 shows a gantry ring positioning unit for translating a gantry in three directions and tilting the gantry with respect to one axis, according to one aspect of the invention.

FIG. 3 shows a schematic diagram of the assembled components of a ring positioning unit 20 in accordance with one embodiment of the invention. Relative motion of the gantry ring is achieved by a set of individual positioners, including an in/out positioner 305, a vertical positioner 307, a lateral positioner 309, and a tilt positioner 311. A Z-bracket 313 is used to rigidly connect the vertical 307, lateral 309, and tilt 311 positioners to the in/out positioner 305.

Figure 4:
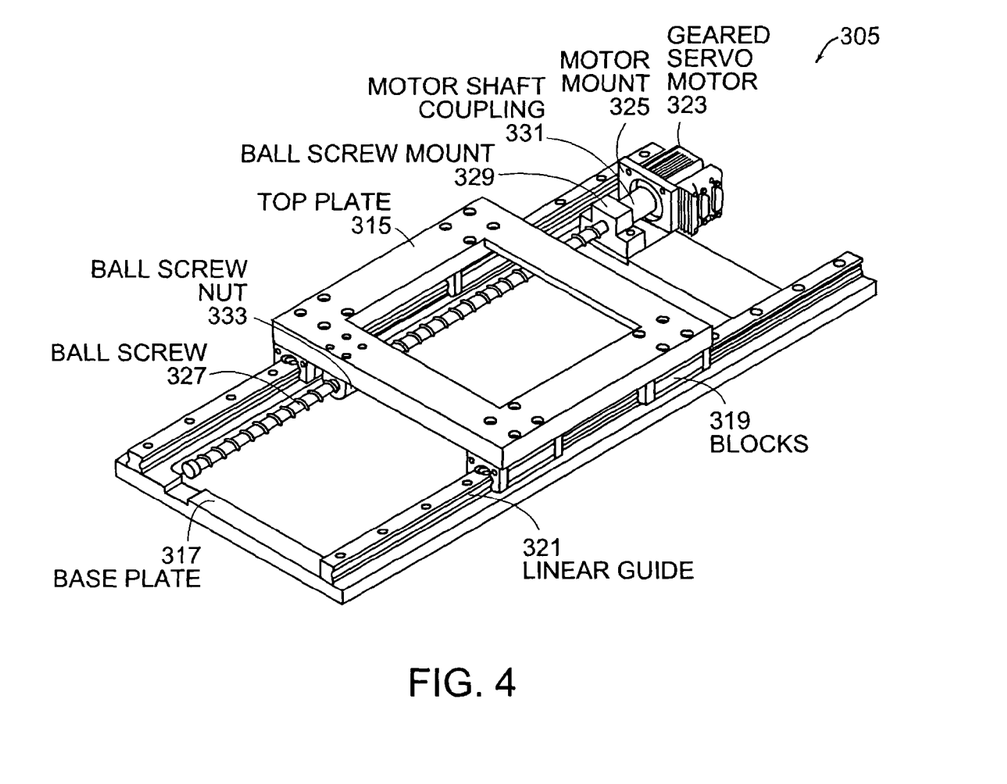
FIG. 4 shows a ring positioning unit for translating the gantry ring in an in/out direction.

Referring now to FIG. 4, the in/out positioner 305 comprises a motorized assembly for translating the cantilevered gantry ring towards or away from the support structure. The in/out positioner includes a top plate 315 upon which the Z-bracket 313 (see FIG. 3) is bolted. The top plate 315 is movable along the length of a base plate 317 via blocks 319 which mate with linear guide rails 321 on the base plate 317. A geared servo motor 323 is rigidly attached to the base plate 317 by a motor mount 325. A ball screw 327 is mounted in ball screw mount 329, and runs along the length of the base plate 317 parallel to linear guide rails 321. The ball screw 327 is mated with a ball screw nut 333 that is fixedly secured to the top plate 315. The motor 323 rotates the ball screw 327 in a clockwise or counterclockwise direction via motor shaft coupling 331. The rotation of the ball screw 327, in either a clockwise or counterclockwise direction, causes the ball screw nut 333, and thus the top plate 315, to travel up and down the length of the ball screw 327. The linear guide and blocks steer the top plate as it is displaced along the length of the base plate 317 by servo motor 323. In this way, the cantilevered gantry assembly can be translated towards or away from the support structure, such as a mobile cart, floor, wall, ceiling, or a patient table, in a controlled manner.

Figure 5:
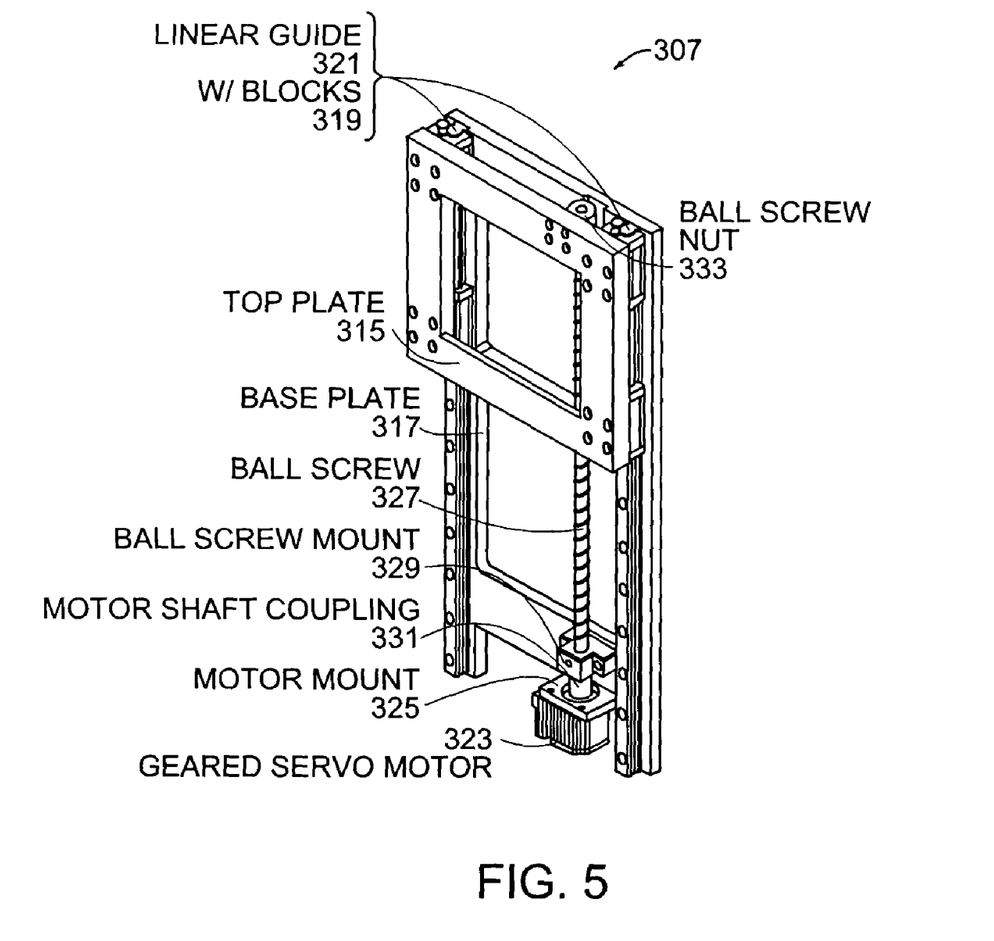
FIG. 5 shows a ring positioning unit for translating the gantry in a vertical direction.

FIG. 5 shows the vertical positioner 307 for translating the generally O-shaped cantilevered gantry vertically relative to the support structure. In the embodiment shown in FIG. 5, the vertical positioner 307 is a motorized assembly that is essentially identical to the in/out positioner 305 in terms of its structure and operation. However, the vertical positioner 307 is oriented vertically so that the top plate can be translated upwards or downwards relative to the base plate. As illustrated in FIG. 5, the vertical positioner includes a top plate 315 movably mounted onto a base plate 317 via blocks 319 which ride on linear guide rails 321. The top plate 315 is translated relative to the base plate 317 by a servo motor 323 and ball screw 327, as described in connection with FIG. 4. As shown in FIG. 3, the top plate of the vertical positioner 307 is rigidly secured to the Z-bracket 313, and the entire Z-bracket assembly is secured to the top plate of the in/out positioner 305. The top plate of the vertical positioner 307 thus remains vertically fixed to Z-bracket, while the base plate of the vertical positioner 307 is capable of translating vertically up and down in a telescoping fashion relative to the Z-bracket and the in/out positioner.

Figure 6:
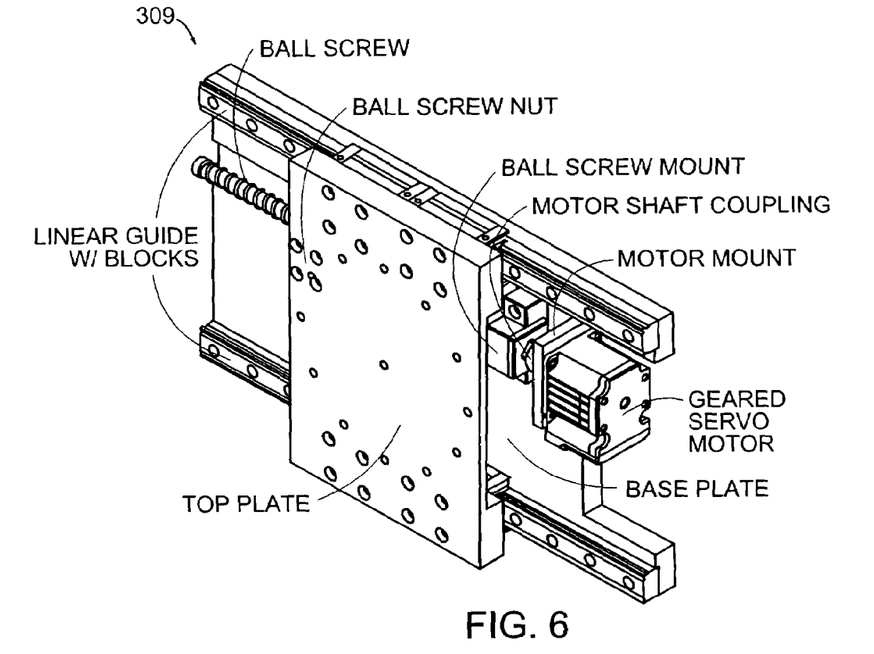
FIG. 6 shows a ring positioning unit for translating the gantry in a lateral direction.

FIG. 6 shows the lateral positioner 309 for translating the generally O-shaped cantilevered gantry in a lateral direction relative to the support structure. In this embodiment, the lateral positioner 309 comprises a motorized assembly that is essentially identical to the previously-described in/out positioner 305 and vertical positioner 307 in terms of its structure and operation. However, the lateral positioner 309 is oriented in a lateral direction so that the top plate can be translated from side to side relative to the base plate. As illustrated in FIG. 6, the lateral positioner includes a top plate 315 movably mounted onto a base plate 317 via blocks 319 which ride on linear guide rails 321. The top plate 315 is translated relative to the base plate 317 by a servo motor 323 and ball screw 327, as described in connection with FIG. 4. As shown in FIG. 3, the base plate of the lateral positioner 309 is rigidly attached to the base plate of the vertical postioner 307. The entire lateral positioner 309 is thus translated in/out or vertically up/down with the respective movements of the in/out positioner 305 and the vertical positioner 307. The top plate of the lateral positioner 309 can be attached to the gantry ring to translate the ring laterally left and right relative to the Z-bracket 313 and the support structure.

Figure 7:
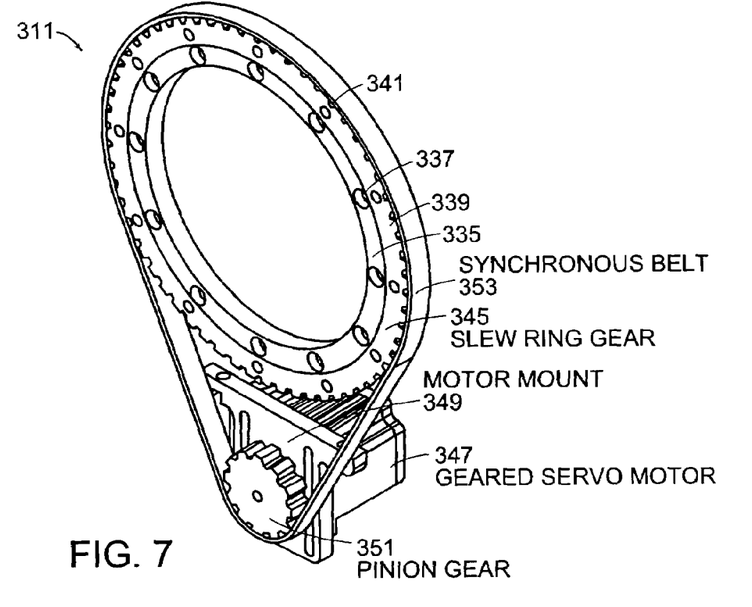
FIG. 7 shows a ring positioning unit for tilting the gantry with respect to one axis.

FIG. 7 shows the tilt positioner 311 for tilting the generally O-shaped cantilevered gantry relative to the support structure. An inner ring 335 includes mounting holes 337 for rigidly attaching the ring to the top plate of the lateral positioner 309. An outer ring 339, larger in diameter than the inner ring 335 includes mounting holes 341 for rigidly attaching the outer ring 339 to the gantry 11. The outer ring 339 includes a gear with external teeth and is rotatable relative to the inner ring 335 on bearings. The complete two-ring assembly is referred to as a slew ring gear 345. A geared servo motor 347, mounted to the lateral positioner 309 by motor mount 349, rotates the slew ring gear 345 via a pinion gear 351 with external teeth and a synchronous belt 353. Rotation of the slew ring gear tilts the cantilevered gantry relative to the lateral positioner, as illustrated in FIG. 2. It will be understood that a tilt positioner such as described in connection with FIG. 7 can be employed to tilt the gantry about any suitable axis. For example, a tilt positioner could be used to join the top plate 315 of the in/out positioner 305 to the Z-bracket to permit the gantry to rotate about the vertical axis.

According to one aspect, each of the positioner assemblies 305, 307, 309, 311 comprising the ring positioning unit 20, includes a mechanism for providing position feedback information to its respective servomotor in order to enable precise positioning of the gantry along each degree of translational or rotational motion. For example, referring to FIG. 4, a linear encoder tape can be affixed to a linear guide rail 321 of the base plate 317, and a read head can be located on a the top plate 315 for reading the encoder tape and providing feedback data indicative of the relative positions of the top plate 315 and the base plate 317. Similarly, in reference to FIG. 7, a rotary encoder can be used to determine the relative angular positions of the inner 335 and outer 339 rings of the slew ring gear 345. Preferably, the position feedback mechanism is an absolute position encoder system, so that, at any given time, a computerized motion control system can precisely determine the translational and/or rotational position of the ring positioning unit in all degrees of freedom, and can thus determine the position and orientation of the gantry in three-dimensional space.

Figure 8:
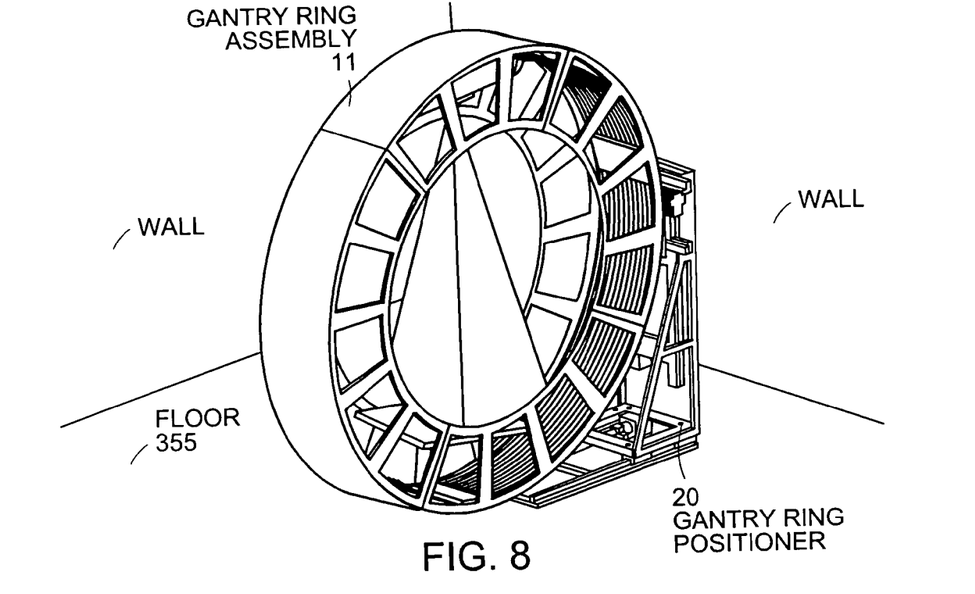
FIG. 8 shows a floor-mounted cantilevered gantry ring with ring positioning unit.
Figure 9:
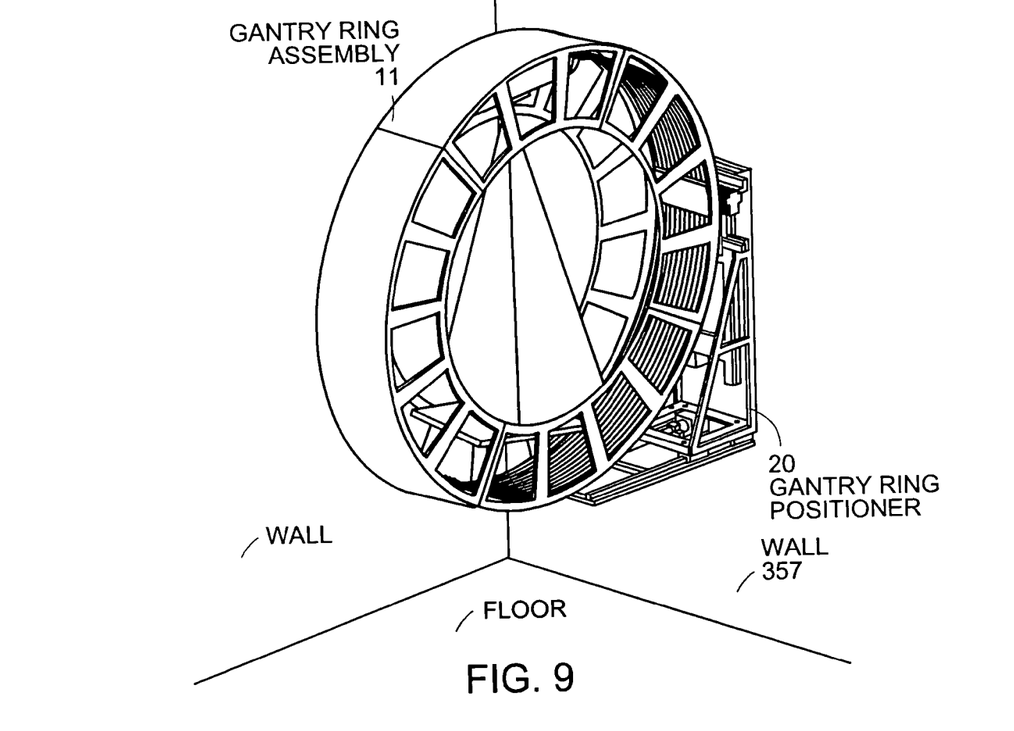
FIG. 9 shows a wall-mounted cantilevered gantry ring with ring positioning unit.
Figure 10:
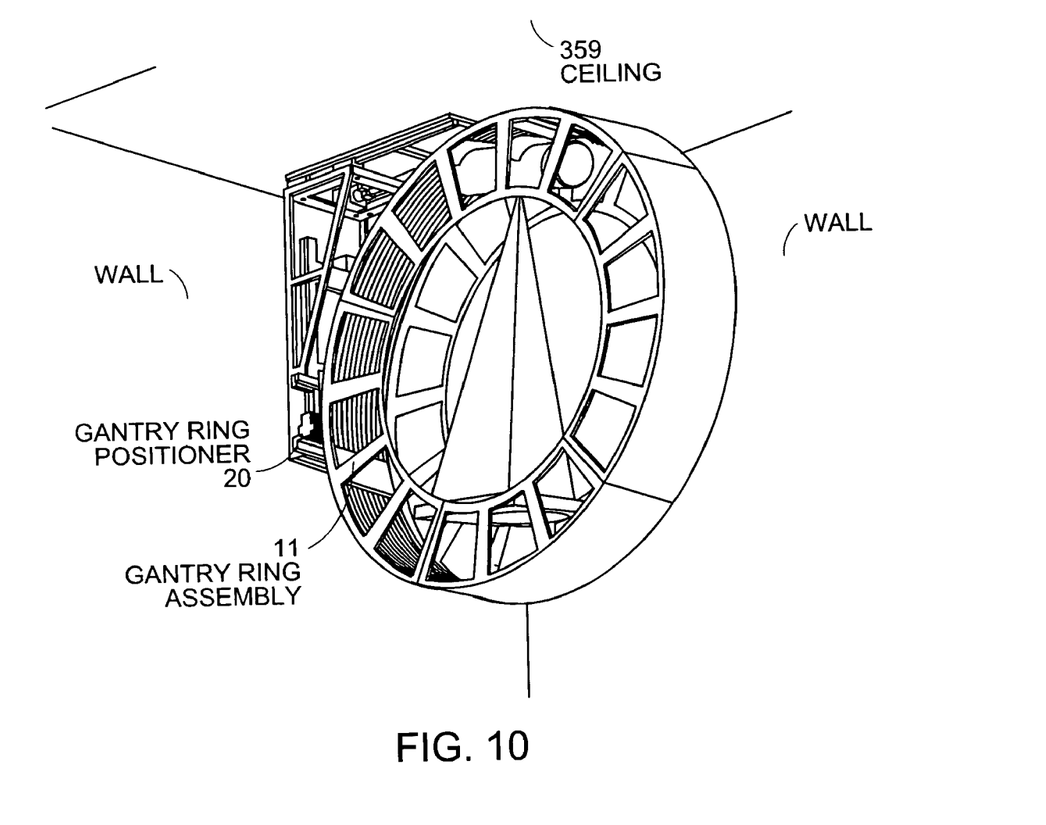
FIG. 10 shows a ceiling-mounted cantilevered gantry ring with ring positioning unit.

Turing now to FIGS. 8–10, various embodiments of a cantilevered O-shaped gantry 11 and ring positioning unit 20 are shown. In FIG. 8, the ring positioning unit 20 is mounted to the floor 355 by the base plate of in/out positioner. The tilt positioner 311 is mounted to one side of the gantry 11. This allows the cantilevered gantry to translate and tilt relative to the fixed room.

FIG. 9 shows the ring positioning unit 20 mounted on one side to a wall 357, and on the other side to the gantry 11, thus allowing the cantilevered gantry to translate and tilt relative to the fixed room. In FIG. 10, the ring positioning unit 20 is fixed on one side to the ceiling 359, and on the other side to the gantry 11. The ring positioning unit 20 and gantry 11 could be similarly mounted to any suitable support structure, such as to a table upon which a patient under examination is placed.

The x-ray imaging systems and methods described herein may be advantageously used for two-dimensional and/or three-dimensional x-ray scanning. Individual two-dimensional projections from set angles along the gantry rotation can be viewed, or multiple projections collected throughout a partial or full rotation may be reconstructed using cone or fan beam tomographic reconstruction techniques. This invention could be used for acquiring multi-planar x-ray images in a quasi-simultaneous manner, such as described in commonly-owned U.S. patent application Ser. No. 10/389, 268, filed on Mar. 13, 2003, the entire teachings of which are incorporated herein by reference.

The detector arrays of the present invention include two-dimensional flat panel solid-state detector arrays. It will be understood, however, that various detectors and detector arrays can be used in this invention, including any detector configurations used in typical diagnostic fan-beam or cone-beam imaging systems, such as C-arm fluoroscopes, or single-sliced or multi-sliced CT scanners, or mobile and fixed-room floroscopy devices which utilize image intensifier technology. A preferred detector is a two-dimensional thin-film transistor x-ray detector using scintillator amorphous-silicon technology.

For large field-of-view imaging, the detector array can be translated to, and acquire imaging data at, two or more positions along a line or arc opposite the x-ray source, such as via a motorized detector rail and bearing system. Examples of such detector systems, and associated beam positioning systems, are described in commonly owned U.S. patent application Ser. No. 10/392,365, filed Mar. 18, 2003, the entire teachings of which are incorporated herein by reference.

In yet another aspect, the O-shaped gantry can include a segment that at least partially detaches from the gantry ring to provide an opening or "break" in the gantry ring through which the object to be imaged may enter and exit the central imaging area of the gantry ring in a radial direction. An advantage of this type of device is the ability to manipulate the x-ray gantry around the target object, such as a patient, and then close the gantry around the object, causing minimal disruption to the object, in order to perform x-ray imaging. Examples of "breakable" gantry devices for x-ray imaging are described in commonly-owned U.S. patent application Ser. No. 10/319,407, filed Dec. 12, 2002, the entire teachings of which are incorporated herein by reference.

While this invention has been particularly shown and described with references to preferred embodiments thereof, it will be understood by those skilled in the art that various changes in form and details may be made therein without departing from the scope of the invention encompassed by the appended claims. For instance, although the particular embodiments shown and described herein relate in general to x-ray imaging applications, it will further be understood that the principles of the present invention may also be extended to other medical and non-medical imaging applications, including, for example, magnetic resonance imaging (MRI), positron emission tomography (PET), single photon emission computed tomography (SPECT), ultrasound imaging, and photographic imaging.

Also, while the embodiments shown and described here relate in general to medical imaging, it will be understood that the invention may be used for numerous other applications, including industrial applications, such as testing and analysis of materials, inspection of containers, and imaging of large objects.

What is claimed is:

1. An imaging apparatus comprising:
   a generally O-shaped gantry ring;
   a radiation source and a radiation detector being housed within the gantry ring, at least one of the source and the detector being rotatable 360 degrees around the interior of the gantry ring, said rotation being independent of any movement of the gantry ring;
   a support structure; and
   a ring positioning unit that attaches to one side of the gantry ring to secures the gantry ring to the support structure in a cantilevered manner, the ring positioning unit positionsing the gantry ring relative to the support structure.

2. The imaging apparatus of claim 1, wherein the ring positioning unit positions the gantry ring by translating the ring in a direction towards or away from the support structure.

3. The imaging apparatus of claim 1, wherein the ring positioning unit positions the gantry ring by translating the ring in a vertical direction relative to the support structure.

4. The imaging apparatus of claim 1, wherein the ring positioning unit positions the gantry ring by translating the ring in a lateral direction relative to the support structure.

5. The imaging apparatus of claim 1, wherein the ring positioning unit positions the gantry ring by rotating the gantry about at least one axis.

6. The imaging apparatus of claim 1, wherein the ring positioning unit positions the gantry ring by translating the gantry ring three perpendicular axes, and rotates the gantry ring about at least one axis.

7. The imaging apparatus of claim 1, wherein the support structure comprises a mobile support structure.

8. The imaging apparatus of claim 1, wherein the support structure comprises a cart.

9. The imaging apparatus of claim 8, wherein the cart is a mobile cart.

10. The imaging apparatus of claim 1, wherein the support structure comprises at least one of a floor, a ceiling, and a wall.

11. The imaging apparatus of claim 1, wherein the imaging system comprises an x-ray imaging system.

12. The imaging apparatus of claim 11, wherein the gantry comprises an x-ray source and a detector array opposed to the source.

13. The imaging apparatus of claim 12, wherein both the x-ray source and the detector array are rotatable around the interior of the gantry.

14. The imaging apparatus of claim 13, wherein both the x-ray source and the detector array are rotatable at least 360 degrees around the interior of the gantry.

15. The imaging apparatus of claim 1, wherein the apparatus is operable to obtain two-dimensional x-ray images of an object.

16. The imaging apparatus of claim 1, wherein the apparatus is operable to obtain three-dimensional computerized tomographic x-ray images of an object.

17. The imaging apparatus of claim 1, wherein a central opening of the generally O-shaped gantry is adapted for positioning a human patient within the opening.

18. The apparatus of claim 1, further comprising a control system which directs the positioning unit to move the gantry to a user-defined position and orientation.

19. The apparatus of claim 18, wherein the control system directs the positioning unit based upon stored positioning information.

20. The apparatus of claim 18, further comprising a position feedback mechanism for determining the position of the gantry relative to the support structure.

21. The imaging apparatus of claim 1, further comprising a ring positioning unit that attaches to one end of the gantry for securing the gantry ring to the mobile support and for moving the gantry ring relative to the mobile support.

22. A method for imaging an object with an imaging system having a substantially O-shaped gantry, the gantry being secured to a support structure at one end in a cantilevered fashion by a ring positioning unit, the method comprising:
    positioning the object within a central opening of the generally O-shaped gantry;
    operating the ring positioning unit to position the gantry at a predetermined position and orientation relative to the support structure;
    rotating at least one of a radiation source and a radiation detector around the interior of the gantry ring, said rotation being independent of any movement of the gantry ring; and
    obtaining an image of the object.

23. The method of claim 22, wherein the ring positioning unit positions the gantry ring by translating the ring in a direction towards or away from the support structure.

24. The imaging apparatus of claim 22, wherein the ring positioning unit positions the gantry ring by translating the ring in a vertical direction relative to the support structure.

25. The imaging apparatus of claim 22, wherein the ring positioning unit positions the gantry ring by translating the ring in a lateral direction relative to the support structure.

26. The imaging apparatus of claim 22, wherein the ring positioning unit positions the gantry ring by rotating the gantry about at least one axis.

27. The imaging apparatus of claim 22, wherein the ring positioning unit positions the gantry ring by translating the gantry ring three perpendicular axes, and rotates the gantry ring about at least one axis.

28. An x-ray imaging apparatus comprising:
    a generally O-shaped gantry ring having a radiation source and a detector array for obtaining two-dimensional or three-dimensional images of an object located within the gantry ring; and a mobile support that supports the gantry at one end of the gantry in a cantilevered fashion.

29. An imaging apparatus, comprising:

a generally O-shaped gantry ring;

means for supporting the gantry ring at one end of the gantry in a cantilevered fashion; and means for positioning the gantry ring relative to the means for supporting.

* * * * *

UNITED STATES PATENT AND TRADEMARK OFFICE
CERTIFICATE OF CORRECTION

PATENT NO. : 7,001,045 B2
DATED : February 21, 2006
INVENTOR(S) : Eugene A. Gregerson, Richard K. Grant and Norbert J. Johnson It is certified that error appears in the above-identified patent and that said Letters Patent is hereby corrected as shown below:

<u>Column 7,</u>
Line 38, replace "ring to secures" with -- ring to secure --.

Signed and Sealed this

Thirtieth Day of May, 2006

JON W. DUDAS
*Director of the United States Patent and Trademark Office*